United States Patent
Nelson et al.

(10) Patent No.: US 11,369,449 B2
(45) Date of Patent: Jun. 28, 2022

(54) MODULAR CABLE-DRIVEN SURGICAL ROBOTS

(71) Applicant: NUtech Ventures, Lincoln, NE (US)

(72) Inventors: Carl A. Nelson, Lincoln, NE (US); Nicholas Nelson, Portland, OR (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 248 days.

(21) Appl. No.: 16/577,230

(22) Filed: Sep. 20, 2019

(65) Prior Publication Data

US 2020/0093553 A1    Mar. 26, 2020

Related U.S. Application Data

(60) Provisional application No. 62/734,208, filed on Sep. 20, 2018.

(51) Int. Cl.
*A61B 34/00*    (2016.01)
*A61B 34/30*    (2016.01)
*A61B 1/00*    (2006.01)

(52) U.S. Cl.
CPC .............. *A61B 34/71* (2016.02); *A61B 34/30* (2016.02); *A61B 1/00149* (2013.01); *A61B 2034/715* (2016.02)

(58) Field of Classification Search
CPC ... A61B 34/71; A61B 34/30; A61B 2034/715; A61B 2034/306; A61B 1/00149;

(Continued)

(56) References Cited

U.S. PATENT DOCUMENTS 8,491,603 B2    7/2013    Yeung et al.
9,096,033 B2    8/2015    Holop et al.
(Continued)

OTHER PUBLICATIONS

Nelson et al., "Design of a Modular, Partially Disposable Robot for Minimally Invasive Surgery," Proceedings of the 2018 Design of Medical Devices Conference, pp. 1-3 (Apr. 9-12, 2018).

(Continued)

*Primary Examiner* — Tan-Uyen T Ho
*Assistant Examiner* — Bridget E. Rabaglia
(74) *Attorney, Agent, or Firm* — Jenkins, Wilson, Taylor & Hunt, P.A.

(57) ABSTRACT

A surgical robot can be configured for minimally invasive surgery (MIS) and other types of surgery with modular link geometry and disposable components. In some examples, the surgical robot includes a cable driver comprising at least one drive motor configured for tensioning a cable. The surgical robot includes an articulated surgical tool coupled to the drive motor by the cable. The articulated surgical tool comprises at least first and second articulated links and a joint coupling the first and second articulated links. The cable passes through the joint, and the joint comprises an elastic antagonist biased in opposition to tension from the cable to allow bidirectional actuation of the joint. The surgical robot includes a safety lock configured to lock the joint from allowing articulation of the first and second articulated links in response to a loss of tension in the cable.

20 Claims, 9 Drawing Sheets

(58) Field of Classification Search
CPC ............... A61B 1/0016; A61B 1/0057; A61B 2017/00318; A61B 2017/00323; A61B 2017/00407
USPC ........................................................ 606/130
See application file for complete search history.

(56) References Cited

U.S. PATENT DOCUMENTS

| | | | |
|---|---|---|---|
| 10,624,708 B2* | 4/2020 | Hunter | A61B 34/71 |
| 2007/0142969 A1 | 6/2007 | Devengenzo et al. | |
| 2011/0282359 A1 | 11/2011 | Duval | |
| 2012/0209253 A1* | 8/2012 | Donhowe | A61B 17/00 606/1 |

OTHER PUBLICATIONS

"Whose Line Is That," Coastal Wind Sports, http://www.coastalwindsports.com/WhoseLine.html, pp. 1-3 (2017).

"Robotic Surgery Infographic," ECRI Institute, https://www.ecri.org/Resources/ASG/Robotic_Surgery_Infographic_MS15369_web.pdf, pp. 1-2 (2015).

Dumpert et al., "Semi-Autonomous Surgical Tasks using a Miniature In Vivo Surgical Robot," Proceedings of the IEEE Engineering in Medicine and Biology Society Conference, pp. 266-269 (Sep. 3-6, 2009).

Lanfranco et al., "Robotic Surgery: A Current Perspective," Annals of Surgery, vol. 239, No. 1, pp. 14-21 (2004).

* cited by examiner

MODULAR CABLE-DRIVEN SURGICAL ROBOTS

PRIORITY CLAIM

This application claims the benefit of U.S. Provisional Application Ser. No. 62/734,208, filed Sep. 20, 2018, the disclosure of which is incorporated herein by reference in its entirety.

GOVERNMENT INTEREST

This invention was made with government support under grant number 1659777 awarded by the National Science Foundation. The government has certain rights to this invention.

BACKGROUND

The subject matter described in this specifically relates generally to surgical robots, e.g., modular cable-driven surgical robots.

The use of robots has been shown to improve outcomes in certain types of surgery (shorter recovery times, reduced complications, etc.) because of the dexterity, precise control, and improved surgeon working posture that they can enable [1]. However, because each type of surgery has its own different requirements (work-space, motion complexity, etc.), robots with limited ability to reconfigure their kinematic characteristics have become narrowly used in certain surgical domains because they were unable to show improved outcomes in surgeries for which they were not optimized. For example, the da Vinci Surgical System (Intuitive Surgical) is perhaps the most well-known and widely used robot, but its use is concentrated in a few types of cases—52% gynecology (hysterectomy most common), 20% urology (nephrectomy and prostatectomy most common), and 24% general surgery (lower and upper GI most common) [2]. Another type of robot, in which a much smaller structure is mostly or fully inserted into the abdominal cavity during surgery [3], can enable a more varied surgical workspace (e.g., can perform large-scale bowel resection) but may not be well suited to other surgery types due to space constraints. Availability of surgical robot technology is also very non-uniform. Roughly three fourths of American hospitals do not own a da Vinci robot, for example. This limits patient access to the technology as well as surgeon access for training, resulting in significant stratification between facilities.

SUMMARY

A surgical robot can be configured for minimally invasive surgery (MIS) and other types of surgery with modular link geometry and disposable components. In some examples, the surgical robot includes a cable driver comprising at least one drive motor configured for tensioning a cable. The surgical robot includes an articulated surgical tool coupled to the drive motor by the cable. The articulated surgical tool comprises at least first and second articulated links and a joint coupling the first and second articulated links. The cable passes through the joint, and the joint comprises an elastic antagonist biased in opposition to tension from the cable to allow bidirectional actuation of the joint. The surgical robot includes a safety lock configured to lock the joint from allowing articulation of the first and second articulated links in response to a loss of tension in the cable.

DETAILED DESCRIPTION

This specification describes modular surgical robots and methods for operating modular surgical robots. The surgical robots are more flexible and reconfigurable compared to some conventional surgical robots, while ensuring human-safe robot interactions. The surgical robots are cable-driven and have modular link and joint designs, enabling a variety of serial configurations. The joint design includes an elastic antagonist (e.g., a biasing spring) which inherently creates a maximum load threshold while also reducing the number of actuating cables by half compared to systems using cables pre-tensioned in pairs like antagonistically acting tendons in order to maintain robot stiffness and allow bidirectional actuation. Safety of this joint mechanism is ensured by a safety lock, e.g., a ratchet-based locking mechanism.

The surgical robots allow the surgeon to customize an appropriate robot configuration for the type of surgery being performed, while incurring reduced cost compared to existing robotic surgical systems. Consider the following possible two advantages of using the surgical robots described in this specification. First, the ability to adapt a robot's fundamental architecture based on modularity would enable the expansion of robotic technology to a much wider variety of surgery types without the need for dedicated robots optimized for each procedure. Second, reducing the complexity of design and manufacture of surgical robots would make them affordable for even small, rural clinics, which would significantly expand and equalize access to high-quality surgical care in the long term (when synergistically paired with ongoing advancements in telepresence and teleoperation). As a result, the surgical robots described in this specification enable low-cost, widespread use of robots to achieve improved surgical outcomes.

Figure 1A:
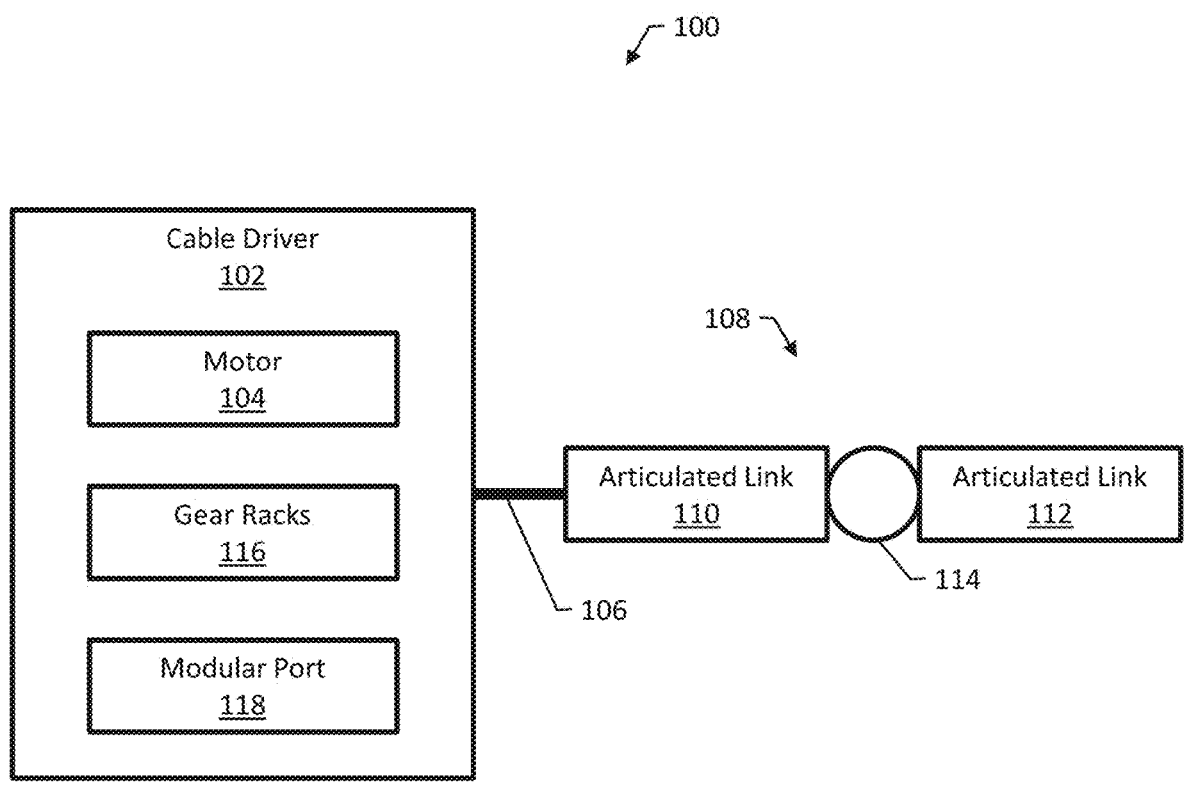
FIGS. 1A-D illustrate an example surgical robot.

FIG. 1A is a block diagram of an example surgical robot 100. The surgical robot 100 includes a cable driver 102 that includes at least one drive motor 104 configured for tensioning a cable 106. The surgical robot 100 also includes an articulated surgical tool 108 coupled to the cable driver 102 by the cable 106.

In some examples, the articulated surgical tool is a modular kit of links and joints, which can be assembled in a variety of configurations, and are driven by cables. To make this robot modularity possible, all the expensive and reusable components (motors, electronics) are moved outside the body, such that the "robot" is reusable indefinitely and the "instrument" controlled by the robot can be, e.g., a single-use device. In contrast, the da Vinci system locates its motors outside the patient, but each inserted instrument (reusable up to 10 times) contains a number of tiny precision-manufactured components (pulleys, pins, etc.) in order to transmit motion and forces to the instrument tip using pre-tensioned stainless steel "wire rope" cables. By using polymeric cables made of Spectra material (a fiber based on ultra-high molecular weight polyethylene made by Honeywell), the cable fatigue concerns are alleviated since the minimum bending radius is much smaller, and the need for precision components to protect the cables is greatly reduced. By weight, this material is 15 times stronger than steel and 40% stronger than Kevlar [4].

As shown in FIG. 1A, the articulated surgical tool 108 includes first and second articulated links 110 and 112. The articulated surgical tool 108 also includes a joint 114 coupling the first and second articulated links 110 and 112. The cable 106 passes through the joint 114. The joint 114 includes an elastic antagonist biased in opposition to tension from the cable to allow bidirectional actuation of the joint 114. The articulated surgical tool 108 includes a safety lock configured to lock the joint 114 from allowing articulation of the first and second articulated links 110 and 112 in response to a loss of tension in the cable 106 (e.g., if the cable 106 breaks or a component holding tension in the cable 106 breaks).

Figure 1B:
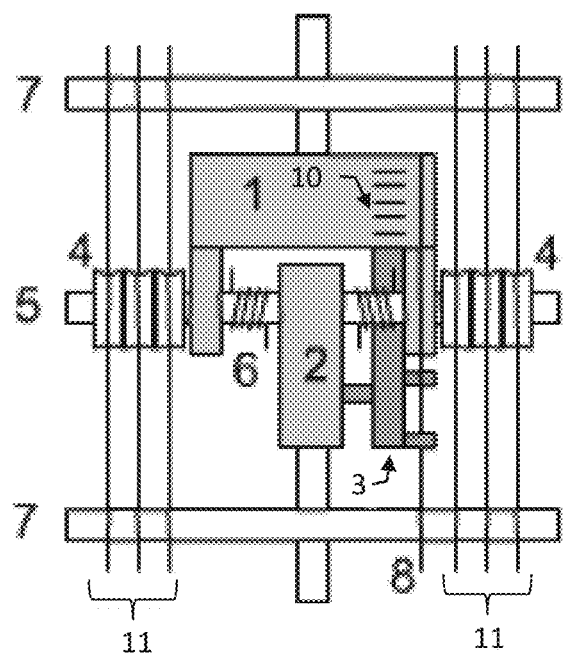
Figure 1C:
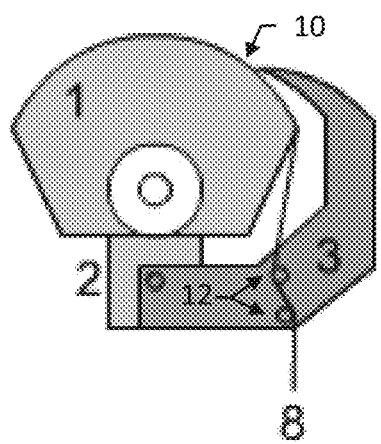
Figure 1D:
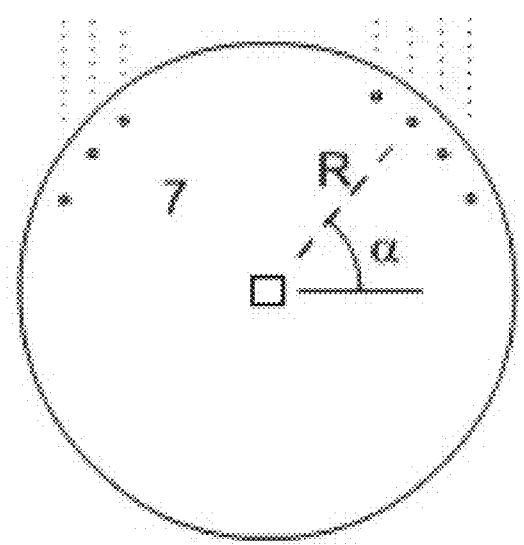

FIGS. 1B-D illustrate an example of the joint 114 including the elastic antagonist as a spring and the safety lock as a pawl and ratchet. The joint, as illustrated in FIGS. 1B-D, is a clevis-and-pin joint with cable routing manifolds. Biasing springs are introduced to reduce the number of control cables by half (down to a single cable per degree of freedom of the instrument).

FIG. 1B shows a top view of the joint. FIG. 1C shows a simplified front view of the joint, and FIG. 1D shows a simplified side view of the joint. The joint includes a first joint half 1 having a ratchet surface 10, a second joint half 2, a pawl 3, pulleys 4, a shaft 5, biasing springs 6, cable routing manifolds 7, and a locking cable 8 and one or more transmission cables 11.

Placing a spring at each robot joint in this manner allows development of relatively more slender, highly articulated instruments. To avoid the sudden unsafe release of stored spring energy in the event of a broken or detached cable, the joint includes a safety lock based on a ratchet and pawl mechanism (shown more clearly in FIG. 1C), whereby loss of tension in any of the transmission cables 11 triggers locking of the corresponding joint; contact of the locking cable 8 against the pawl 3 creates a moment which pulls the pawl 3 out of contact with the ratchet surface 10. As shown in FIG. 1C, the pawl 3 includes a pair of guides 12 (e.g., raised pins), and the locking cable 8 is routed between the pair of raised pins to pull the pawl 3 out of contact with the ratchet surface 10.

Referring back to FIG. 1A, in some examples, the cable driver 102 includes sliding gear racks 116. The gear racks 116 can slide, e.g., on linear tracks to tension the cable 106. The linear tracks are parallel linear tracks in some examples. The cable driver 102 can also include a modular port 118 configured for receiving the articulated surgical tool 108 and coupling the cable 106 from within the articulated surgical tool 108 to the sliding gear racks 116.

A standardized cable routing manifold guides the control cables along the serial robot structure. Using a standardized manifold on each link allows the links to be made in different sizes and shapes, for customization of the robot configuration, while keeping the components low-cost (due to the choice of cable material, these components can have relatively simple geometry and be made of plastic). Straight and 90-degree links, along with the manifold/joint units able to be reoriented in increments of 90 degrees, allow all three primary axis orientations for the robot arm (pitch, yaw, and roll).

Figure 2A:
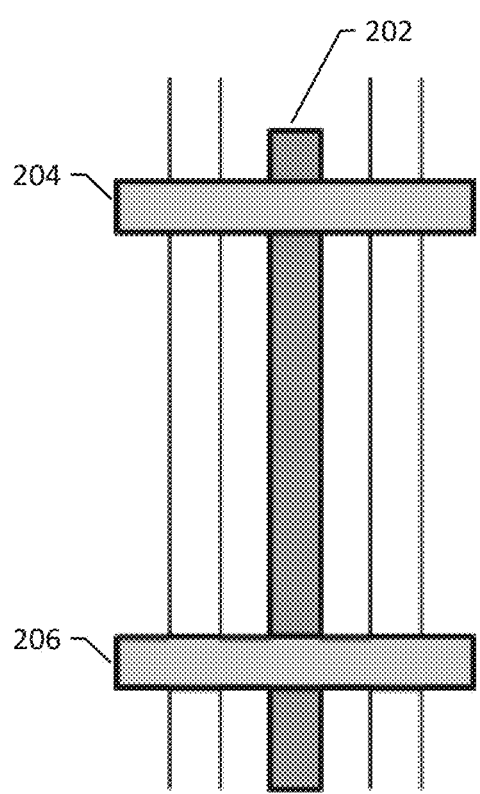
FIGS. 2A-B illustrate two examples of link and manifold orientations to enable different joint axis orientations.
Figure 2B:
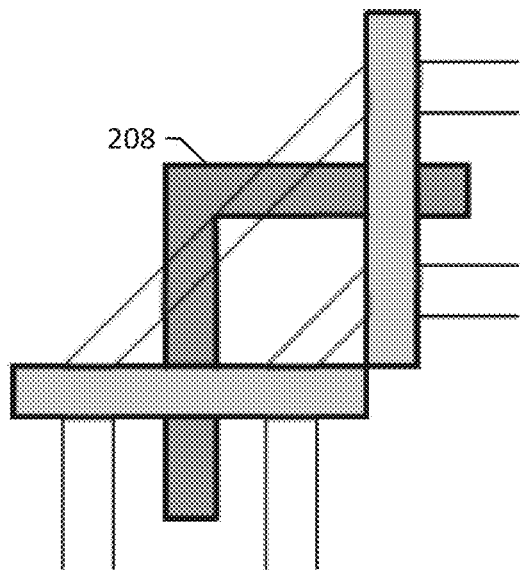

FIGS. 2A-B illustrate two examples of link and manifold orientations to enable different joint axis orientations. FIG. 2A shows a straight link 202 and cable manifolds 204 and 206 crossing over the straight link 202. FIG. 2B shows a right-angled link 208.

Figure 3:
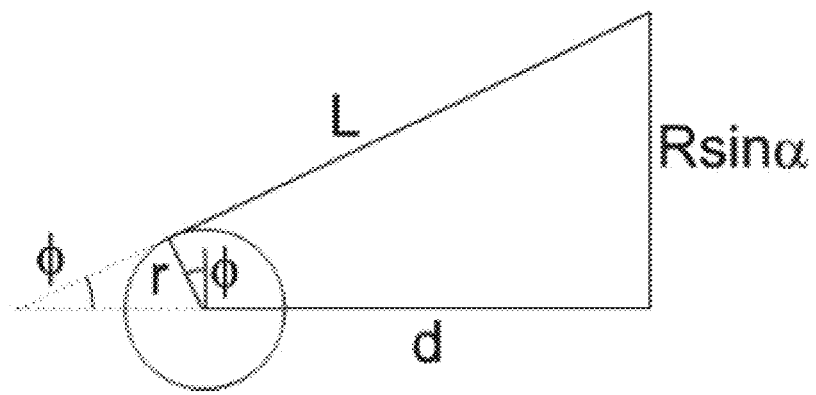
FIG. 3 illustrates the geometry describing cable length, pulley wrapping, and routing manifold.

FIG. 3 illustrates the geometry describing cable length, pulley wrapping, and routing manifold. Referring to FIG. 3, and using the notation indicated therein, the cable length L between the cable manifold and the point of tangency on the pulley of radius r is dependent on the angle of the cable which produces that tangency. Closure of a vector loop in the vertical and horizontal directions gives $$L \sin(\phi) + r \cos(\phi) = R \sin(\alpha) \quad (1)$$

$$L \cos(\phi) - r \sin(\phi) = d \quad (2)$$

where R is the radius of the hole pattern in the cable manifold, $\alpha$ is the angular position of the cable in the manifold (as indicated in FIG. 1D), and d is the distance from the manifold center to the joint center. Combining these two equations gives $$L^2 = R \sin(\alpha)\sin(\phi) + d \cos(\phi) \quad (3)$$

$$r^2 = R \sin(\alpha)\cos(\phi) - d \sin(\phi) \quad (4)$$

and the latter is readily solved for $\phi$ using Freudenstein's method and the tangent half-angle identity [5].

Figure 4:
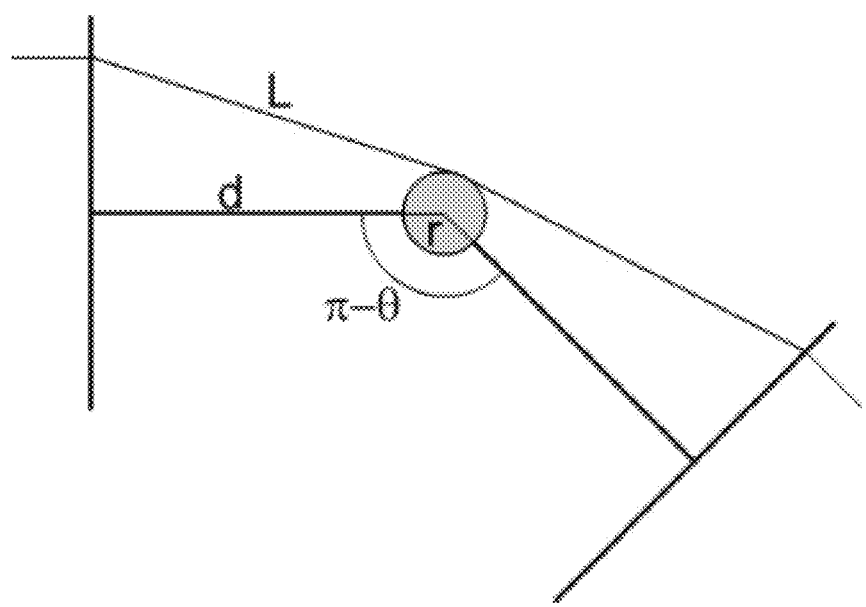
FIG. 4 illustrates the geometry relating joint angle to cable wrapping and lengths between manifolds.

Note that the cable length L in FIG. 3 is not dependent on the joint angle which we will call $\theta$. FIG. 4 illustrates the geometry relating joint angle to cable wrapping and lengths between manifolds. Using the construction of FIG. 4, the relation between the joint angle and the total cable length across the joint is $$L_{total} = L_{prox} + r(2\pi + \theta - \phi_{prox} - \phi_{dist}) + L_{dist} \quad (5)$$

where the subscripts prox and dist refer to the cable length and angle on the proximal and distal sides of the joint respectively, and the middle term represents the length of cable wrapped around the pulley. As previously noted, L and $\phi$ are not a function of $\theta$, so the input/output relationship between cable payout and joint angle is linear as in the middle term of (5), i.e., $r\theta$.

It is important for the cables entering a joint from a manifold to align with their respective pulleys. Based on a uniform pulley width $w_p$, and with pulleys stacked side by side as in FIG. 1 (pulleys labeled as item 4), groupings of cable holes in the manifold should be laid out such that $$w_p = R(\cos(\alpha_i) - \cos(\alpha_{i-1})) \quad (6)$$

is constant, where the $i^{th}$ and $i-1^{st}$ cable holes are adjacent. This is for cables being passed through a joint (i.e., actuating a more distal joint). For an actuating cable having a wrap radius $\rho$ on the clevis link of the joint (shown as the round profile on item 1 in FIG. 1B), and based on the angular dependency in (5), the overall cable length input $C_n$ for the $n^{th}$ joint (measured relative to a neutral or "home" position of the robot) is $$C_n = \rho_n \theta_n + \Sigma_{i=1}^{n-1} r_i \theta_i \qquad (7)$$

where joint 1 is the most proximal joint in the serial robot, and values of $\theta_i$ can be determined from the desired pose and the inverse kinematics of the particular robot configuration.

Figure 5:
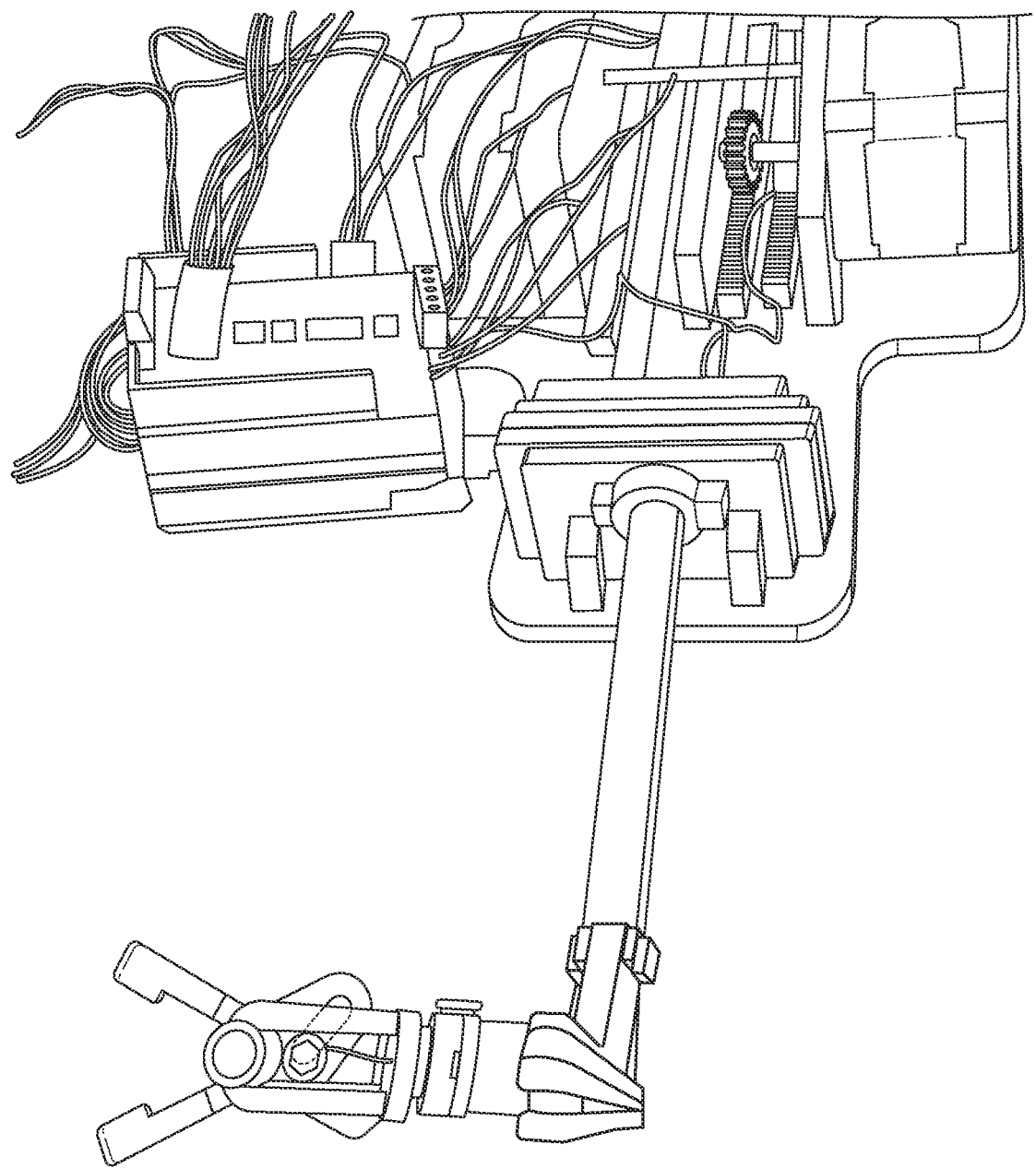
FIG. 5 shows a robot prototype with cables passing through joint axes.

FIG. 5 shows a robot prototype with cables passing through joint axes. The robot was fabricated using a combination of laser cutting and 3D printing, and is shown in FIG. 5. To decouple the robot kinematics, the routing manifolds were designed with r=0, α=0 (cables aligned through joint axes) and various values of R in this case. However, this resulted in inefficient use of space near the joint, and the robot lacked the ratchet-based safety mechanism.

Figure 6A:
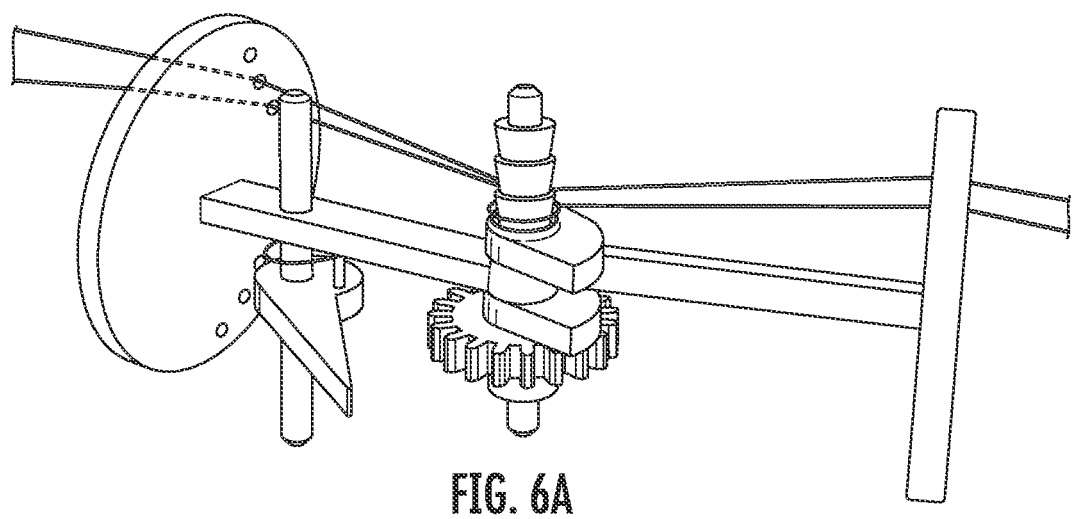
FIG. 6 shows a prototype of a joint made in acrylic using a laser cutting process.
Figure 6B:
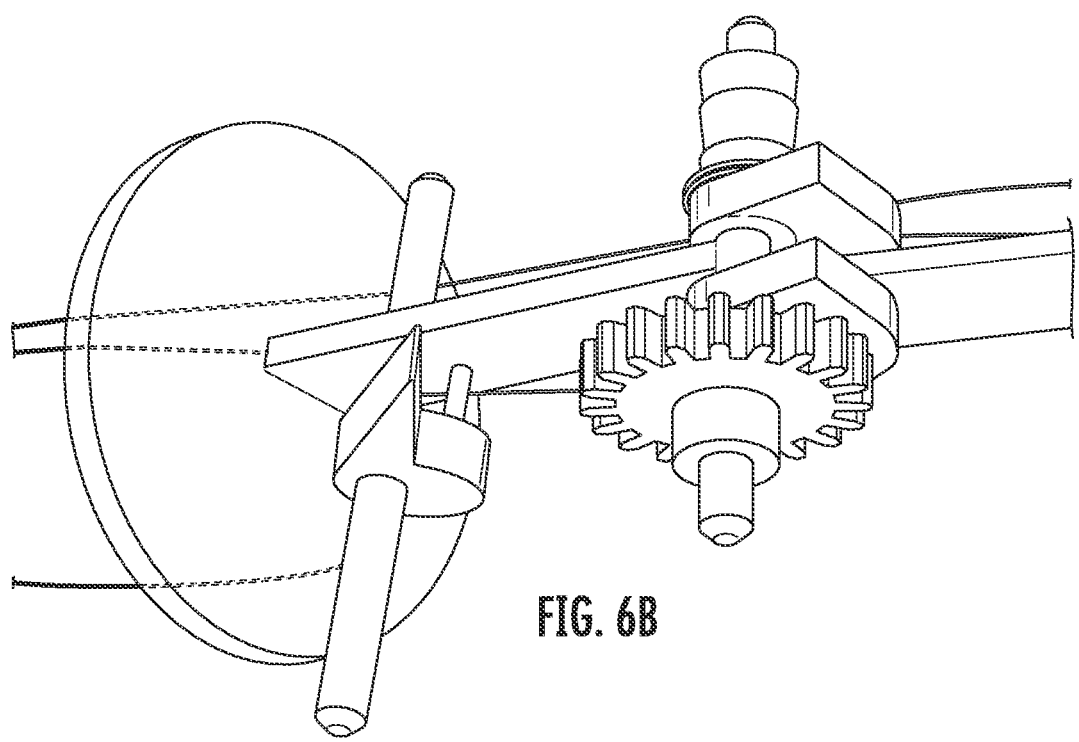

FIG. 6 shows a prototype of a joint made in acrylic using a laser cutting process. This scaled version successfully demonstrated the functionality of the cable routing and the safety mechanism. It was also found that a more efficient use of space could be achieved by locating a linear biasing spring in the unused space adjacent to the routing manifold, rather than using a torsion spring on the joint shaft itself. FIG. 6 shows how cable tension disengages the locking mechanism via contact with the pin inserted through the pawl component.

Figure 7:
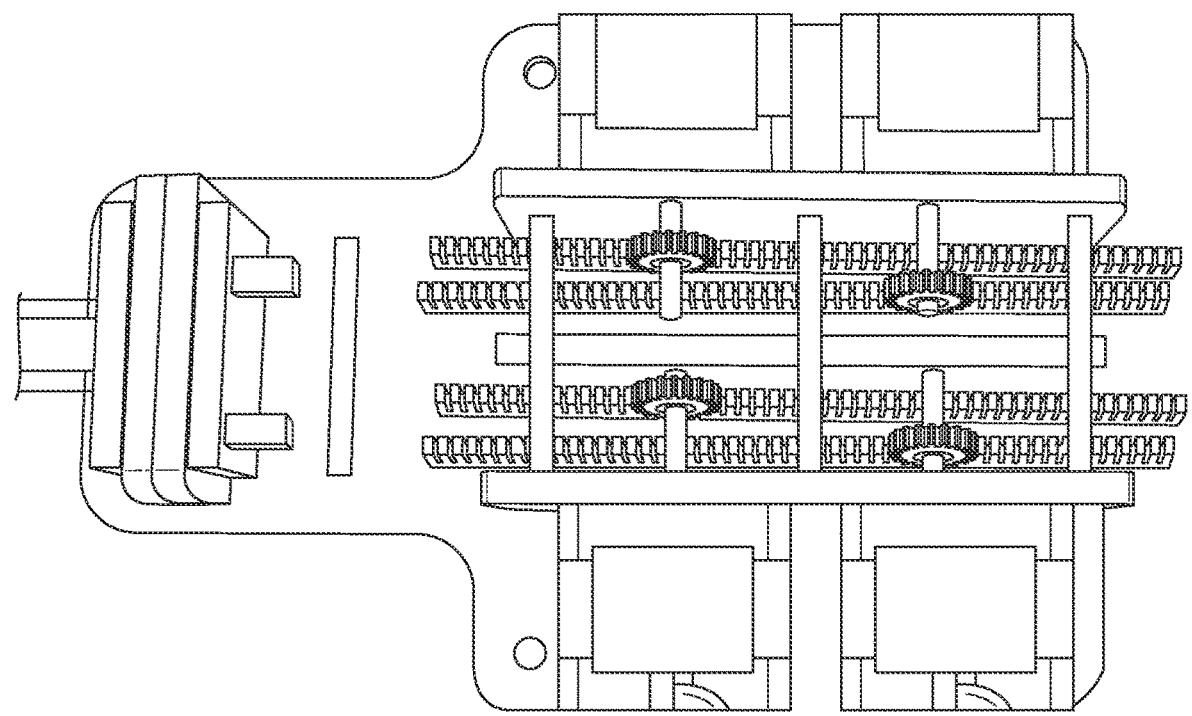
FIG. 7 shows an example cable driver including gear racks for cable actuation.

FIG. 7 shows an example cable driver including gear racks for cable actuation. The cable driver is designed for simplicity and modularity. Gear racks on parallel linear tracks are driven by gears on the motor shafts to actuate the cables.

Figure 8:
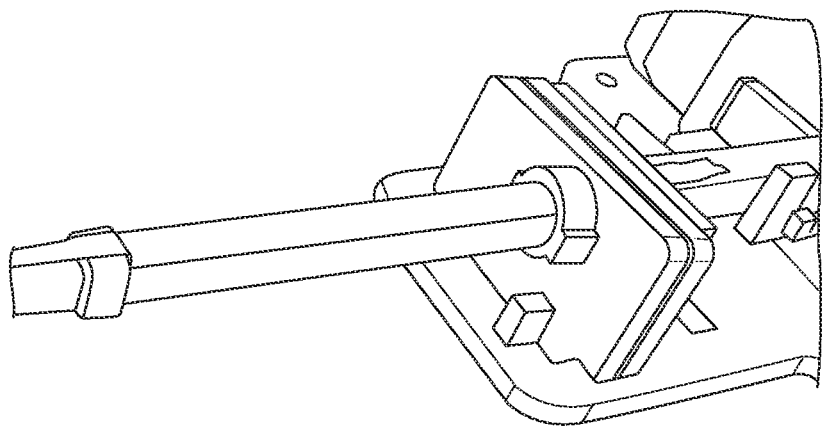
FIG. 8 shows an example modular port connecting an articulated surgical tool to the cable driver.

FIG. 8 shows an example modular port connecting an articulated surgical tool to the cable driver. The modular port allows the robotic articulation and instrument tip to be attached and driven by the motor package. Different cable-driven tools can be adapted to this port and quickly swapped in/out. Interfacing the kinematic control simply requires slipping cable end-loops over the hooked ends of the gear racks. This increases the tool's ability to be inexpensive and disposable. This also allows for different types of tool arms, configured with different kinematics, to be interchanged when needed.

Figure 9:
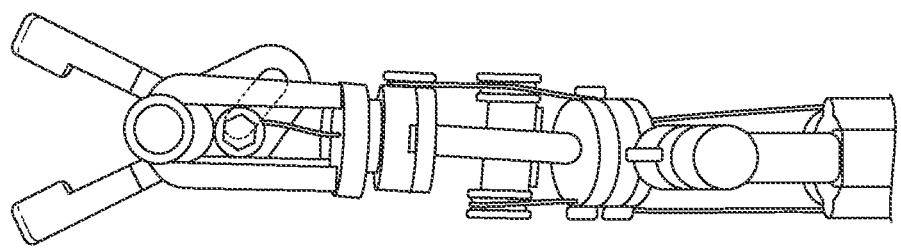
FIG. 9 shows an example tool arm with a cable routing manifold.

FIG. 9 shows an example tool arm with a cable routing manifold. The routing manifold directs cables at each rotational join of the robotic articulation such that cable tensions pass through or near the axis of rotation and do not produce coupled joint moments.

A prototype robot was implemented with three degrees of freedom (pitch, yaw, and roll) and a simple grasper instrument tip. Each of these degrees of freedom are operated via one motor actuating one cable, permitting simple control and setup of the tool arm and reducing the number of cables by half compared to typical cable driven robots. The cable used in this prototype was common braided fishing line, which was strong and did not strain noticeably under tension. Each cable's actuation is counteracted by an elastic antagonist component, either elastic bands in the pitch and yaw or small torsion springs in the roll and grasp. These antagonists retain tension in the cables when the motors reverse to release tension on the cables. This eliminates the need for complex cable tensioners within the tool arm. The elastic bands were chosen as an inexpensive and disposable method of counteracting cable tension.

In some examples, elastic bands may be easier to reduce in size along with the rest of the device compared to torsion springs. Most of the components were laser cut in acrylic or 3D-printed in acrylonitrile butadiene styrene (ABS). The overall outer diameter of the robotic instrument was 18 mm. Proof-of-concept testing was performed using a benchtop power supply, an Arduino microcontroller with a joystick pad for control, and grasping on various small objects.

The functionality of the prototype shows that the design elements implemented with the goals of modularity and inexpensive design can create a functional device. The gear-rack motor package effectively provides linear actuation to the cables, providing sufficient power to transmit motion in the various degrees of freedom on the tool arm of the device.

The modular tool arm port allows for simple and quick placement and removal of the tool arm to interface with the motor package. During testing, the tool arm of the device frequently needed to be attached and removed as adjustments and iterations were implemented. The application of the modular port made this easy, validating its practicality as a component.

The pitch, yaw, and roll degrees of freedom operated as intended. The pitch and yaw, which function mechanically the same, both rotate around their axes in a 180-degree arc. The elastic bands were shown to be effective when tensioned properly in the device's construction.

In some examples, the device is intended to be used once before being disposed of, which can alleviate concerns regarding fatigue of the elastic bands. The bands did not fail when they were tensioned within a viable range. The adhesive that was used to apply the bands to the plastic of the joint also reduced the compliance of the bands, and failure was avoided by applying minimal amounts of the adhesive. The roll joint was able to rotate 270 degrees around its axis without damage to the small torsion spring. This degree of freedom did not fail during any tests.

The design elements implemented in this proof-of-concept device have shown to be effective, having an interchangeable tool arm system that would permit its use in a broader spectrum of surgical procedures than other devices currently on the market. The design approach emphasizing degrees of freedom operated by single cables, simple mechanical systems in the tool arm, and the external motor package will allow the device's tool arm to be inexpensive, disposable, and easily replaceable while the more expensive, electronic components remain external to the patient and reusable.

Figure 10:
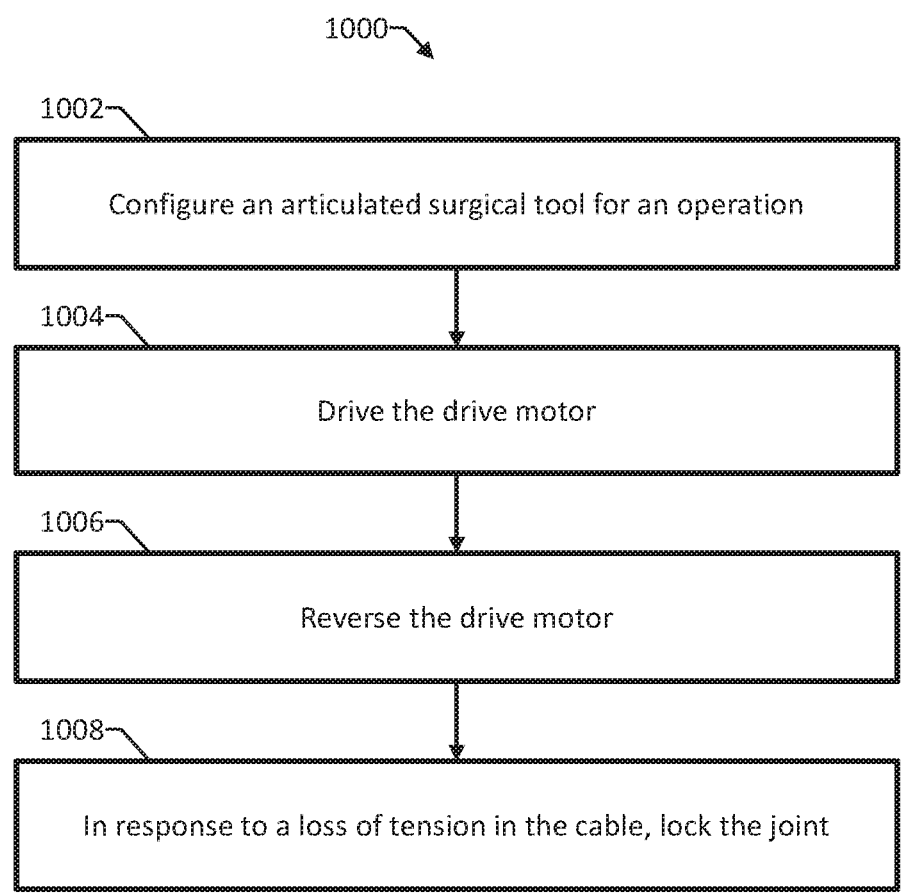
FIG. 10 is a flow diagram of an example method for operating a surgical robot.

FIG. 10 is a flow diagram of an example method 1000 for operating a surgical robot, e.g., the robot 100 of FIG. 1. The method 1000 includes configuring an articulated surgical tool for an operation (1002). For example, articulated links may be assembled into a serial order for a particular operation. In some examples, the articulated surgical tool is designed as a single-use tool and is manufactured such that the only configuration required is attaching the articulated surgical tool to a cable driver, e.g., using a modular port. The articulated surgical tool can then be inserted as appropriate, leaving a cable driver outside the body.

The method 1000 includes driving a drive motor (1004) and reversing the drive motor (1006) to perform an operation. Driving and reversing the drive motor causes an articulated link to rotate about a joint in a first rotational direction and a second rotational direction opposite the first rotational direction. The method 1000 includes, in response to a loss of tension in the cable, locking the joint from allowing articulation of the articulated link, thereby preventing an elastic antagonist from causing sudden, unanticipated movement of the articulated surgical tool (1008).

Various combinations and sub-combinations of the structures and features described in this specification are contemplated and will be apparent to a skilled person having knowledge of this disclosure. Any of the various features and elements as disclosed in this specification may be combined with one or more other disclosed features and elements unless indicated to the contrary.

Correspondingly, the subject matter as claimed is intended to be broadly construed and interpreted, as including all such variations, modifications and alternative embodiments, within its scope and including equivalents of the claims. It is understood that various details of the presently disclosed subject matter may be changed without departing from the scope of the claims. Furthermore, the foregoing description is for the purpose of illustration only, and not for the purpose of limitation.

REFERENCES

1. Lanfranco, A. R., Castellanos, A. E., Desai, J. P., Meyers, W. C.: "Robotic Surgery: A Cur-rent Perspective," Annals of Surgery 239(1):14-21 (2004)
2. ECRI Institute: "Robotic Surgery Infographic," accessed Jan. 5, 2017 at https://www.ecri.org/Resources/ASG/Robotic_Surgery_Infographic_MS1536 9_web.pdf (2017)
3. Dumpert, J., Lehman, A. C., Wood, N. A., Oleynikov, D., Farritor, S. M.: "Semi-Autonomous Surgical Tasks using a Miniature In Vivo Surgical Robot," Proceedings of the IEEE Engi-neering in Medicine and Biology Society Conference, Minneapolis, Minn., September 3-6 (2009)
4. Coastal Wind Sports: "Whose Line Is That," accessed Jan. 5, 2017 at http://www.coastalwindsports.com/Whose-Line.html (2017)
5. Mabie, H. H., Reinholtz, C. F.: Mechanisms and Dynamics of Machinery, 4th ed. Wiley (1984)
6. Nelson, N., Nelson, C. A.: "Design of a Modular, Partially Disposable Robot for Minimally Invasive Surgery," ASME Design of Medical Devices Conference, Minneapolis, Minn., April 10-12 (2018)

What is claimed is:

1. A surgical robot comprising:
a cable driver comprising at least one drive motor configured for tensioning a locking cable; and
an articulated surgical tool coupled to the cable driver by the locking cable, the articulated surgical tool comprising:
at least first and second articulated links;
a joint coupling the first and second articulated links, wherein the locking cable passes through the joint and the joint comprises an elastic antagonist biased in opposition to tension from the locking cable to allow bidirectional actuation of the joint; and
a safety lock configured to lock the joint from allowing articulation of the first and second articulated links in response to a loss of tension in the locking cable.

2. The surgical robot of claim 1, wherein the safety lock comprises a pawl and a ratchet surface.

3. The surgical robot of claim 2, wherein the locking cable is in contact with the pawl creating a force or moment that pulls the pawl out of contact with the ratchet surface, and wherein the safety lock is configured to lock the joint by virtue of allowing the pawl to contact with the ratchet surface in response to the loss of tension in the locking cable.

4. The surgical robot of claim 3, wherein the pawl comprises a pair of guides, and wherein the locking cable is routed between the pair of guides to pull the pawl out of contact with the ratchet surface.

5. The surgical robot of claim 1, wherein the joint comprises a clevis-and-pin joint.

6. The surgical robot of claim 1, wherein the joint comprises a first joint half, a second joint half, a shaft, and one or more pulleys configured to rotate with the shaft, and wherein one or more transmission cables are routed along the one or more pulleys.

7. The surgical robot of claim 1, wherein the elastic antagonist comprises a biasing spring.

8. The surgical robot of claim 1, wherein the elastic antagonist comprises one or more elastic bands.

9. The surgical robot of claim 1, wherein each of the first and second articulated links comprises a cable routing manifold and one or more transmission cables are routed through each of the cable routing manifolds.

10. The surgical robot of claim 1, wherein the cable driver comprises a plurality of sliding gear racks on linear tracks to tension the locking cable and a modular port configured for receiving the articulated surgical tool and coupling the locking cable from within the articulated surgical tool to the sliding gear racks.

11. A method for operating a surgical robot, the method comprising:
driving at least one drive motor of a cable driver, thereby tensioning a locking cable coupled to an articulated surgical tool, wherein the articulated surgical tool comprises at least first and second articulated links and a joint coupling the first and second articulated links, wherein the locking cable passes through the joint and the joint comprises an elastic antagonist biased in opposition to tension from the locking cable, and wherein tensioning the locking cable causes the first articulated link to rotate about the joint in a first rotational direction;
reversing the drive motor, thereby releasing tension from the locking cable and causing the elastic antagonist to rotate the first articulated link about the joint in a second rotational direction opposite the first rotation direction.

12. The method of claim 11, further comprising, in response to a loss of tension in the locking cable, locking the joint from allowing articulation of the first and second articulated links.

13. The method of claim 12, wherein the locking cable is in contact with a pawl, creating a force or moment that pulls the pawl out of contact with a ratchet surface, and wherein locking the joint comprises allowing the pawl to contact the ratchet surface in response to the loss of tension in the locking cable.

14. The method of claim 13, wherein the pawl comprises a pair of guides, and wherein the locking cable is routed between the pair of guides to pull the pawl out of contact with the ratchet surface.

15. The method of claim 11, wherein the joint comprises a first joint half, a second joint half, a shaft, and one or more pulleys configured to rotate with the shaft, and wherein one or more transmission cables are routed along the one or more pulleys.

16. The method of claim 11, wherein the elastic antagonist comprises a biasing spring.

17. The method of claim 11, wherein each of the first and second articulated links comprises a cable routing manifold and one or more transmission cables are routed through each of the cable routing manifolds.

18. The method of claim 11, wherein the cable driver comprises a plurality of sliding gear racks on linear tracks to tension the locking cable and a modular port configured for receiving the articulated surgical tool.

19. The method of claim 18, comprising coupling the locking cable from within the articulated surgical tool to the sliding gear racks.

20. A surgical robot comprising:
- a cable driver comprising at least one drive motor configured for tensioning a cable; and
- an articulated surgical tool coupled to the cable driver by the cable, the articulated surgical tool comprising:
  - at least first and second articulated links; and
  - a joint coupling the first and second articulated links, wherein the cable passes through the joint and the joint comprises an elastic antagonist biased in opposition to tension from the cable to allow bidirectional actuation of the joint.

* * * * *